(12) United States Patent
Shapley et al.

(10) Patent No.: US 10,449,290 B2
(45) Date of Patent: Oct. 22, 2019

(54) THERAPEUTIC PRODUCT DELIVERY DEVICE

(71) Applicant: Cellnovo Limited, Swansea (GB)

(72) Inventors: Julian Shapley, Swansea (GB); Matthew Powell, Swansea (GB); Ceri Clatworthy, Swansea (GB); Joseph Cefai, Swansea (GB)

(73) Assignee: INSULET NETHERLANDS B.V., Schiphol (NL)

( * ) Notice: Subject to any disclaimer, the term of this patent is extended or adjusted under 35 U.S.C. 154(b) by 269 days.

(21) Appl. No.: 15/114,840

(22) PCT Filed: Jan. 30, 2015

(86) PCT No.: PCT/GB2015/050251
§ 371 (c)(1),
(2) Date: Jul. 27, 2016

(87) PCT Pub. No.: WO2015/114373
PCT Pub. Date: Aug. 6, 2015

(65) Prior Publication Data
US 2016/0339170 A1 Nov. 24, 2016

(30) Foreign Application Priority Data
Jan. 30, 2014 (GB) .................................. 1401587.9

(51) Int. Cl.
*A61M 5/142* (2006.01)
*A61M 5/20* (2006.01)
(Continued)

(52) U.S. Cl.
CPC ..... *A61M 5/14244* (2013.01); *A61B 5/14532* (2013.01); *A61M 5/2033* (2013.01);
(Continued)

(58) Field of Classification Search
CPC .... A61M 5/2033; A61M 5/50; A61M 5/5086; A61M 2205/273; A61M 2205/27; A61M 2005/2073; A61M 2005/14268
See application file for complete search history.

(56) References Cited

U.S. PATENT DOCUMENTS 8,454,557 B1 6/2013 Qi et al.
2004/0085215 A1 5/2004 Moberg et al.
(Continued)

FOREIGN PATENT DOCUMENTS

GB 2443261 4/2008
GB 1401587.9 1/2014
(Continued)

OTHER PUBLICATIONS

U.K. Intellectual Property Office, GB Application No. GB 1401587.9, "Search Report under Section 17(5)", dated Aug. 11, 2015, 3 pages.
(Continued)

*Primary Examiner* — Nathan R Price
*Assistant Examiner* — Anh Bui
(74) *Attorney, Agent, or Firm* — Kang S. Lim

(57) ABSTRACT

A therapeutic product delivery device is described which comprises a device body and a cartridge for holding a therapeutic product. An engagement structure is provided for releasably engaging the cartridge with the device body. A fault detector is provided for detecting a fault in the delivery of the therapeutic product from the cartridge. A release trigger is responsive to the detection of a fault to cause the engagement structure to release the cartridge from the device body. In this way, a fault causes the cartridge to be released from the device body, which will prevent any further delivery of the therapeutic product to the patient. This solution is strongly preferable to a solution in which a product delivery mechanism (e.g. a pump) is merely paused or stopped, since when the cartridge separates then no further delivery is possible at all, until the cartridge is reattached (or more probably replaced with a new cartridge in case the fault is with the cartridge).

9 Claims, 4 Drawing Sheets

(51) Int. Cl.
*A61M 5/50* (2006.01)
*A61M 5/315* (2006.01)
*A61B 5/145* (2006.01)
*G06F 19/00* (2018.01)
*A61M 5/24* (2006.01)

(52) U.S. Cl.
CPC .......... *A61M 5/31546* (2013.01); *A61M 5/50* (2013.01); *A61M 5/5086* (2013.01); *G06F 19/3468* (2013.01); *A61M 2005/14268* (2013.01); *A61M 2005/2073* (2013.01); *A61M 2005/244* (2013.01); *A61M 2205/121* (2013.01); *A61M 2205/123* (2013.01); *A61M 2205/27* (2013.01); *A61M 2205/273* (2013.01); *A61M 2205/3584* (2013.01); *A61M 2205/3592* (2013.01); *A61M 2230/201* (2013.01)

(56) References Cited

U.S. PATENT DOCUMENTS

| | | |
|---|---|---|
| 2007/0191770 A1 | 8/2007 | Moberg et al. |
| 2010/0094251 A1* | 4/2010 | Estes ................ A61M 5/14244 604/504 |
| 2010/0137784 A1 | 6/2010 | Cefai et al. |
| 2011/0316562 A1 | 12/2011 | Cefai et al. |
| 2014/0114277 A1* | 4/2014 | Eggert .................. A61M 5/20 604/500 |

FOREIGN PATENT DOCUMENTS

| | | |
|---|---|---|
| WO | WO 2008/024814 | 2/2008 |
| WO | WO 2009/032399 | 3/2009 |
| WO | WO 2010/031059 | 3/2010 |
| WO | WO 2010/078434 | 7/2010 |
| WO | WO 2010/146579 | 12/2010 |
| WO | WO 2011/133823 | 10/2011 |

OTHER PUBLICATIONS

European Patent Office, "Notification of Transmittal of the ISR and the Written Opinion of the International Searching Authority, or the Declaration," in PCT Application No. PCT/GB2015/050251, dated Jun. 12, 2015, 10 pages.

Essen Patent and Trademark Office, letter from the State Intellectual Property of China , "CN Official Examination Notice Summary" in CN Application No. 201580005880.4, dated Apr. 3, 2019, 7 pages.

Translation of Japanese Notice of Refusal, "Notification of Reasons for Refusal" in JP Application No. 2016-548379, dated Oct. 18, 2018, 7 pages.

\* cited by examiner

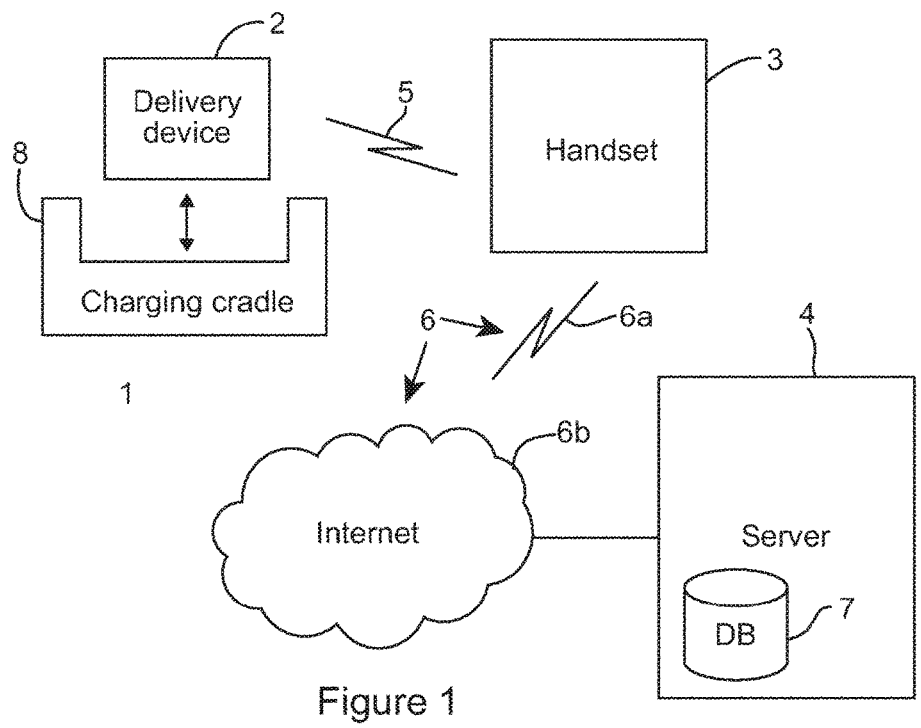
Figure 1
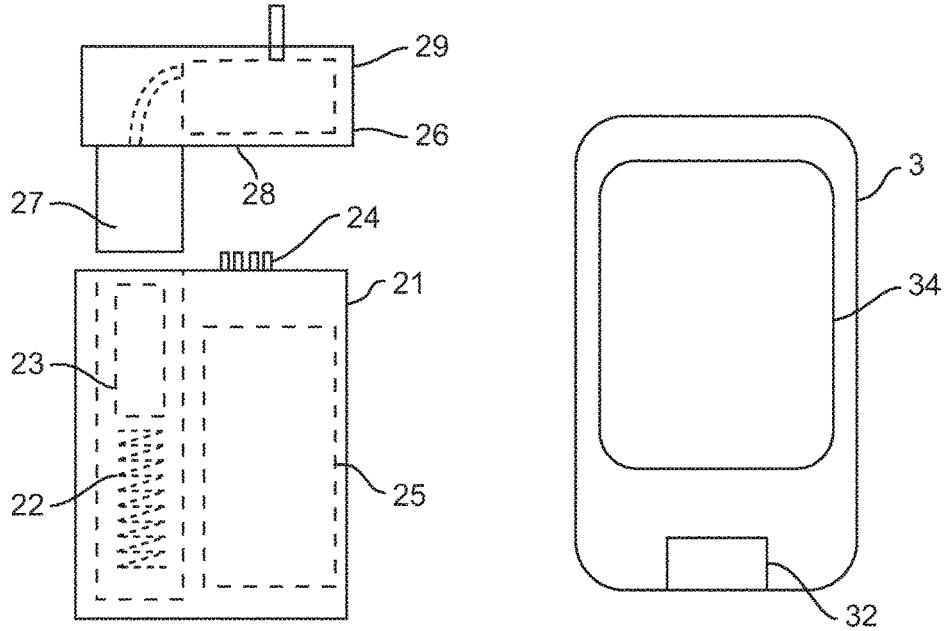
Figure 2
Figure 3

THERAPEUTIC PRODUCT DELIVERY DEVICE

CROSS-REFERENCE TO RELATED APPLICATIONS

The present application is a United States National Stage entry under 35 U.S.C. § 371 of International Application No. PCT/GB2015/050251 filed Jan. 30, 2015, designating the United States of America and published in English on Aug. 6, 2015, which in turn claims priority to Great Britain Application No. 1401587.9, filed Jan. 30, 2014, each of which is incorporated herein by reference in their entirety.

FIELD OF THE INVENTION

The present invention relates to a therapeutic product delivery device.

BACKGROUND TO THE INVENTION

Conventionally, Type 1 diabetes has been treated with daily insulin injections. However, this inevitably results in insulin levels that do not match the normal and rapid changes in blood glucose which occur in a patient throughout the day. On the one hand, insufficient insulin and high glucose levels lead to immediate symptoms and contribute to long-term complications. On the other hand, too much insulin may result in too little blood sugar leading to loss of consciousness and convulsions. As an alternative to injections, insulin pump therapy is intended to mimic the normal physiology of the healthy pancreas. Unlike multiple daily insulin injections, an insulin pump is able to provide a constant background infusion of insulin that can be adjusted according to individual need, compensating for daily activity and exercise routines. The pump may also be programmed to deliver bolus doses of insulin to address the big glucose swings in the blood that would otherwise result from eating and drinking. By mimicking the natural physiology of the pancreas, insulin pump therapy aims to maintain a constantly normal blood glucose level; avoiding the highs that are associated with meals or the lows that come from too much insulin.

There are a number of challenges in providing such a system, including how to address the risk of uncontrolled over-delivery of the insulin into the patient's body in the event of a fault with the delivery device.

Embodiments of the present invention seek to address these problems.

SUMMARY OF THE INVENTION

According to an aspect of the present invention, there is provided a therapeutic product delivery device comprising:
 a device body;
 a cartridge for holding a therapeutic product;
 an engagement structure for releasably engaging the cartridge with the device body;
 a fault detector for detecting a fault in the delivery of the therapeutic product from the cartridge; and
 a release trigger, responsive to the detection of a fault to cause the engagement structure to release the cartridge from the device body.

In this way, a fault causes the cartridge to be released from the device body, which will prevent any further delivery of the therapeutic product to the patient. This solution is strongly preferable to a solution in which a product delivery mechanism (e.g. a pump) is merely paused or stopped, since when the cartridge separates then no further delivery is possible at all, until the cartridge is reattached (or more probably replaced with a new cartridge in case the fault is with the cartridge).

The cartridge may comprises a reservoir containing the therapeutic product and a pumping device for pumping the therapeutic product from the reservoir to the patient. The device body may comprise a battery for powering the pumping device. By separating the cartridge from the device body, the battery is no longer able to supply power to the pumping device, thereby ensuring that the pumping device is no longer able to deliver the therapeutic product to the patient.

The device body may comprise a biasing element which presses against the reservoir of the cartridge when the cartridge is engaged with the device body. The force exerted by the biasing element on the cartridge may in this case cause the cartridge to be ejected away from the device body when the engagement structure releases the cartridge from the device body. As a result, there is no need to provide for a dedicated structure for separating the cartridge from the device body—the biasing means which forms part of the delivery mechanism is able to provide this secondary function. Preferably, the biasing element comprises a spring.

The engagement structure may comprise one or more first engaging elements on one or other of the device body and the cartridge, the first engaging elements being engagable with one or more corresponding second engaging elements on the other of the device body and the cartridge. The first engaging elements may be clips, and the second engaging elements may be lugs. It will be appreciated that other engaging elements may be used instead.

The engagement structure may comprise a releasing element which is moveable between a retaining position in which the first engaging elements are able to engage the second engaging elements, and a releasing position in which the first engaging elements are not able to engage with the second engaging elements, and a wire element which is deformable in response to an applied electric current to move the releasing element from the retaining position to the releasing position. In this case, the release trigger is responsive to the detection of the fault to apply an electric current to the wire element, thereby deforming the wire element. The engagement structure may also comprise a spring which biases the releasing element towards the retaining position, the wire element acting against the bias in response to the applied electric current to move the releasing element into the releasing position. This particular engagement structure has been found to perform effectively with the biasing element to permit the cartridge to be released. Due to the interaction between the spring and the wire element, only a small force, and therefore a relatively low amount of electric power, is required in order to move the releasing element from the retaining position to the releasing position.

In addition to the use of the releasing element in the event of a fault being detected, a release actuator may be provided, which is responsive to user manipulation to move the releasing element from the retaining position to the releasing position. In this way, a cartridge can be manually released in order to replace an empty cartridge with a full cartridge.

While various different faults could be detected, preferably the fault detector detects a fault when the rate of delivery of the therapeutic product exceeds a predetermined threshold rate. It will be appreciated that several different detection methods could be used. However, in one example where the biasing element presses against a movable element of the reservoir, the fault detector comprises a displacement sensor for detecting a position of the movable element, and detection circuitry for detecting a fault when the position of the movable element changes at a rate above a predetermined threshold rate.

DETAILED DESCRIPTION

The invention will now be described by way of example with reference to the following Figures in which:

FIG. 1 shows a schematic view of a drug delivery system;

FIG. 2 shows a schematic view of a drug delivery device;

FIG. 3 shows a schematic view of a handset for controlling the drug delivery device of FIG. 2;

Figure 4A:
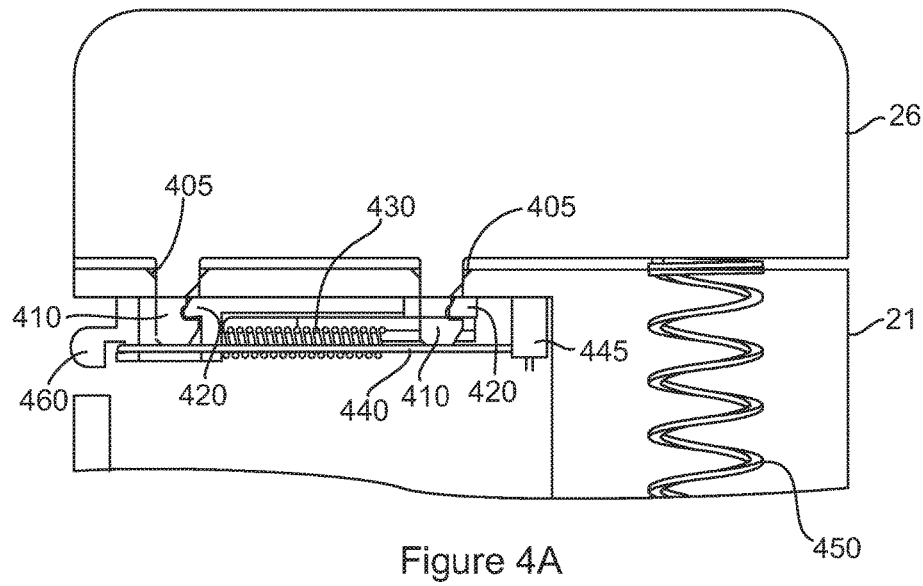
Figure 4B:
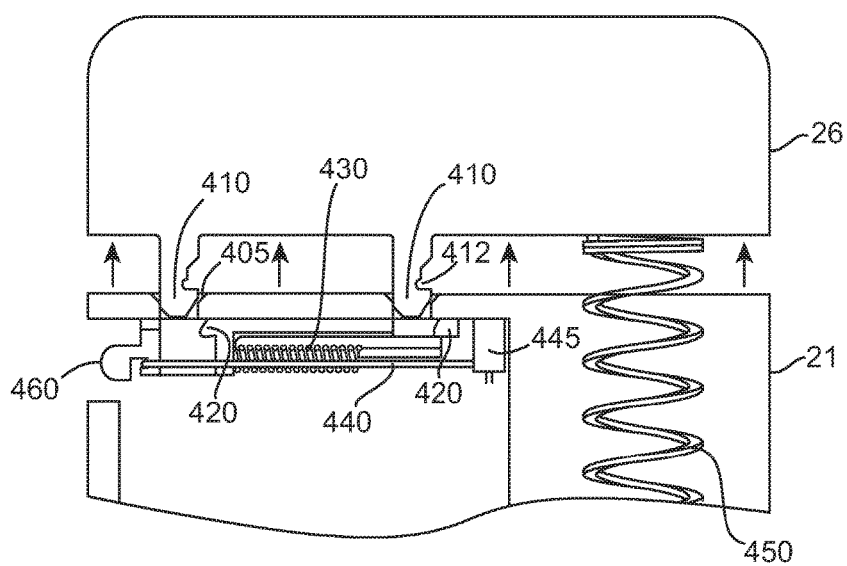
Figure 5A:
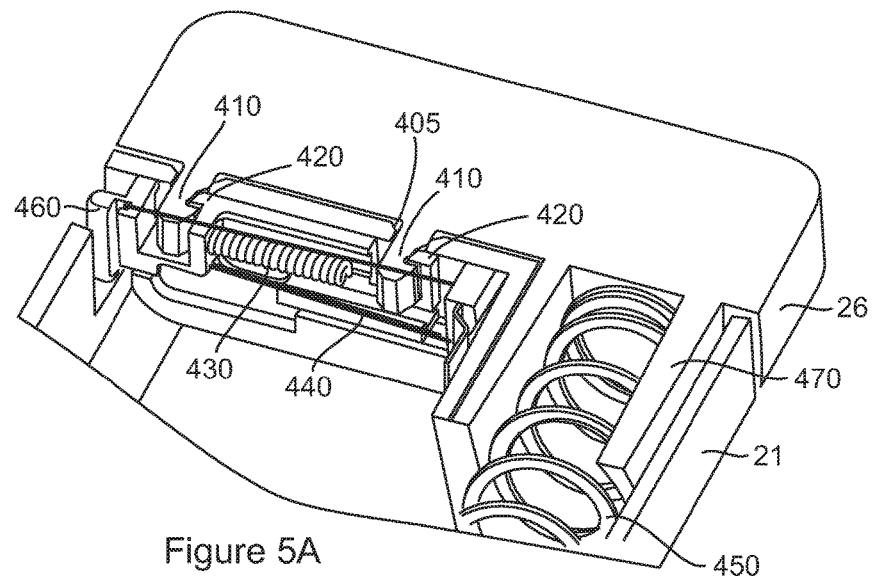
Figure 5B:
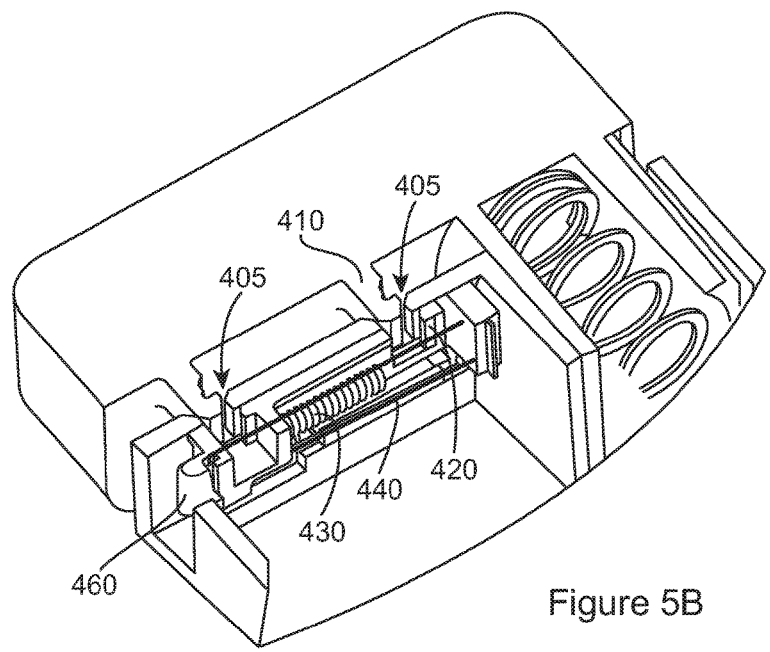
Figure 6:
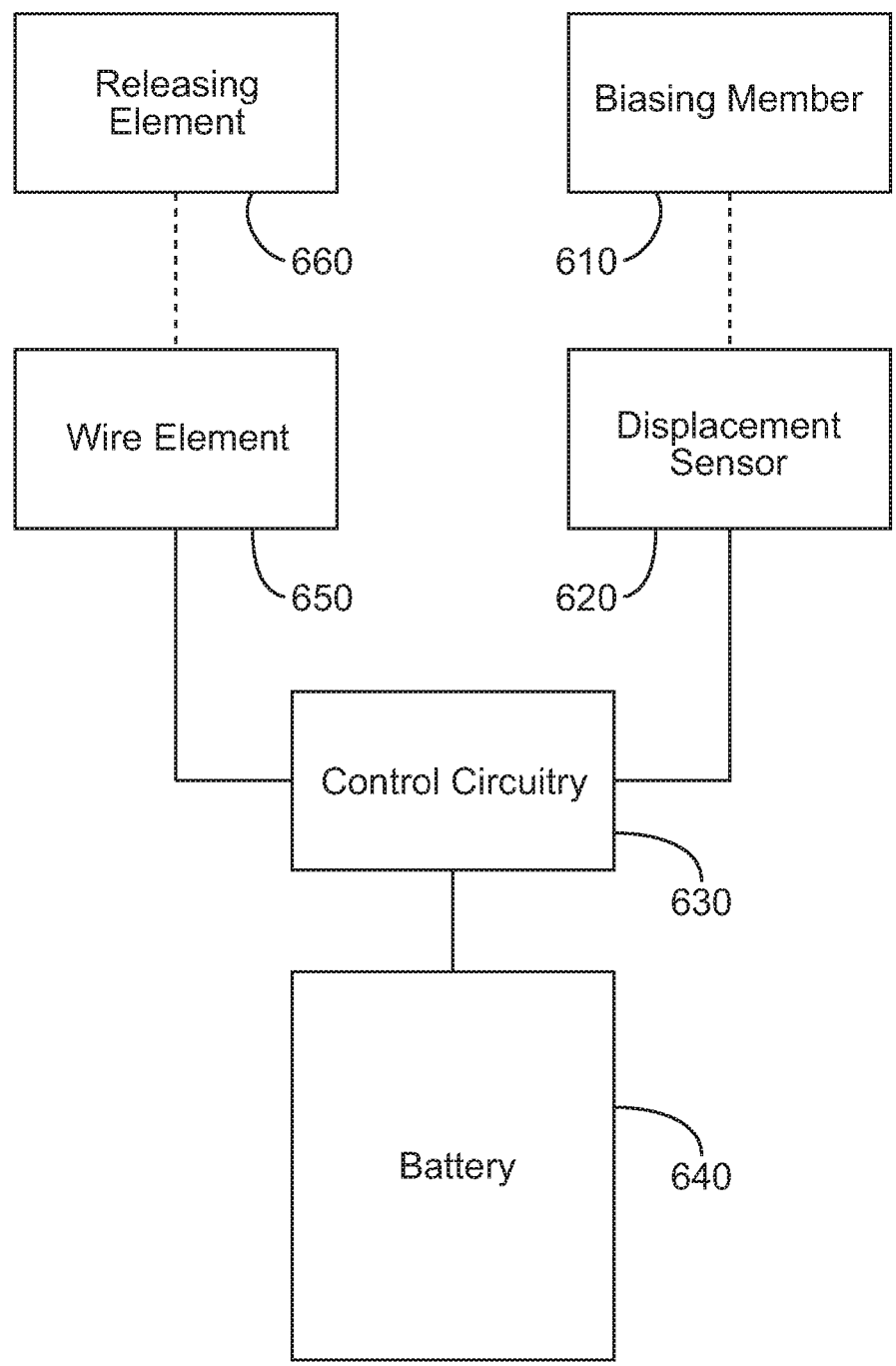

FIGS. 4A and 4B schematically illustrate a release mechanism for the delivery device in retained and released positions;

FIGS. 5A and 5B schematically illustrates the release mechanism of FIGS. 4A and 4B from another view; and FIG. 6 schematically illustrates the ejection of the cartridge based on the detection of a fault.

SYSTEM

Referring to FIG. 1, a drug delivery system 1 is schematically illustrated. The drug delivery system 1 in this case delivers insulin to a patient. However, it will be appreciated that embodiments of the present invention may be appropriate for delivering drugs other than insulin. The system 1 comprises a delivery device 2 which is worn on the patient's body, a handset 3 (which may appear similar to a smartphone) for controlling the delivery device 2, and a server 4. The delivery device 2 and the handset 3 are able to communicate via a first wireless connection 5, for example a lower power ANT radio connection. The handset 3 and the server 4 are able to communicate via a second wireless connection 6, for example a GPRS mobile data connection 6a and the Internet 6b. The server 4 comprises a patient database 7 for storing patient medical information and other information about the patient. Both the delivery device 2 and the handset 3 are powered by rechargeable batteries. Also shown in FIG. 1 is a charging cradle 8 into which the delivery device 2 is inserted in order to charge the delivery device 2.

Delivery Device

The delivery device comprises two parts, which are detachable from each other, as shown schematically in FIG. 2. The first of the two parts is a body 21, which contains a spring 22, a biasing member 23 including a displacement sensor (for example as described in US2011/0316562), and a set of contact pins 24 for providing an electrical connection with the second part. The body 21 also comprises a battery, control circuitry and a transceiver for communicating with the handset, which are not separately shown in FIG. 2 in the interests of clarity, but are generally represented by element 25. The second of the two parts is a disposable insulin cartridge 26, which comprises a reservoir 27 of insulin, contact pads 28 for providing an electrical connection with the body 21 via the pins 24, a pumping device (a wax actuator, for example as described in GB2443261) for pumping the insulin from the reservoir 27 into the patient's body, and a valve arrangement (for example as described in US2010/0137784). The pumping device and valve arrangement are not separately shown in FIG. 2 in the interests of clarity, but are generally represented by element 29. It will be understood that the body 21 of the delivery device is reusable, while the disposable cartridge 26 is intended to be removed and disposed of when the reservoir 27 has been depleted, or when the cartridge has passed its use by date, or if it develops a fault. A new cartridge can then be engaged with the body 21. While it is preferable that the cartridge is disposable, it will be appreciated that, in principle, the cartridge may be refilled and reused again rather than being disposed of. However, even in this case the cartridge should be removable from the body so that a new (full) cartridge can be used while the original cartridge is being refilled.

In use, the body 21 and the cartridge 26 of the delivery device 2 are physically and electrically connected. The electrical connection is via the pins 24 and pads 28. The physical connection may be provided by clips or any other releasable engagement mechanism (not shown). The control circuitry in the body 21 is responsive to control signals received from the handset 3 via the wireless connection 5 to draw current from the battery and apply an electrical current via the pins 24 and the pads 28 to activate the pumping device within the cartridge 26 to draw fluid from the reservoir 27 through the valve arrangement and out of the delivery device 2 to a patient's body. The rate of delivery of the therapeutic product can be controlled by the control circuitry to achieve a particular basal delivery rate, or bolus dose, by controlling the amount and timing of electrical current to the pumping device. Although the basal rate is set by the handset, once set the delivery device 2 is able to maintain the set basal rate with no further communication from the handset 3. As can be seen in FIG. 2, when the body 21 and the cartridge 26 are in engagement, the reservoir 27 is received within the body 21, displacing the biasing member (and displacement sensor) 23 and compressing the spring 22. The compressed spring applies a biasing force to a base of the reservoir 27 via the biasing member 23. The biasing force does not in isolation force insulin from the reservoir 27 through the valve arrangement and into the patient's body, but when combined with the pumping action of the pumping device, the biasing force pressurises the insulin in the reservoir 27 to refill a pumping chamber in advance of each pumping action. It is the pumping action which drives a controlled amount of insulin from the pumping chamber through an outlet valve and to the patient's body. The reservoir takes the form of a cylinder having a first end from which insulin is drawn under the action of the pump, and a second end opposite to the first end at which the (moveable) base is provided. The base of the reservoir moves inwardly of the reservoir (to effectively decrease the size of the reservoir) as the insulin is pumped from the reservoir, under the biasing force provided by the biasing member 23. The position of the biasing member 23 is dependent on the current fill state of the reservoir—that is, how much insulin is remaining in the reservoir. The position of the biasing member 23, and thus the base of the reservoir 27, is determined by the displacement sensor. The displacement sensor is therefore able to generate a signal indicative of the remaining quantity of insulin in the reservoir. By monitoring the change in the remaining quantity of insulin with respect to time, an actual rate of insulin delivery can be determined. This can be used by the control circuitry to apply corrections to the actual delivery rate by adapting the amount and/or timing of electrical current to the pumping device. The quantity of insulin remaining in the reservoir is transmitted to the handset 3, where it can be displayed to the patient and used as an indicator of when the patient should change the current cartridge for a new cartridge. The control circuitry in the body 21 may also transmit an indication of current battery level to the handset, so that the patient is made aware of when the battery requires recharging.

The delivery device also contains an activity monitor to track exercise (not shown). Exercise can have a significant effect on the amount of insulin needed for good control, so tracking exercise accurately is an important part of effective diabetes management. The activity monitor uses a sensor in the delivery device to detect movement of the delivery device, which can be used to infer when the user is engaged in physical activity. The detected activity is then wirelessly communicated to the handset via the wireless connection 5, where the handset (and the server) is able to track and record the patient's activity. Through an online portal to the server, the patient and permitted medical professionals are able to compare activity peaks with blood glucose to identify how activity is influencing the patient's need for insulin. This can in turn be used to program the handset with appropriate dosages for the patient.

Due to the fact that the patient interfaces with the handset rather than the delivery device itself, the delivery device is able to be made small and discreet, and is provided without buttons or a physical connection to a control unit.

Handset

The handset 3 comprises two transceivers. The first transceiver is for communicating with the delivery device via the first wireless connection 5, while the second transceiver is for communicating with the server 4 via the second wireless connection 6. The handset also comprises a processor for running control software. The control software monitors the patient's condition and reports it to the central server 4, and controls the delivery of insulin doses to the patient by transmitting control signals to the delivery device 2. The handset 3 also comprises a touch screen display 34, which displays information to the user and provides a user interface for the user to input data, modify the basal rate, and trigger extraordinary bolas doses.

As well as wirelessly controlling the pump, the handset 3 also has an integral blood glucose meter 32. The blood glucose meter 32 detects the amount of glucose in the patient's blood. The blood may be analysed at the meter 32 by pricking the patient's finger and depositing a droplet of blood on a slide, which is inserted into the meter 32. The detected blood glucose level can be brought to the attention of the patient on the handset 3, and the patient can decide to trigger a bolas dose based on the blood glucose information. The result of every blood glucose test is automatically logged by the software and becomes immediately available for reference via the server 4 to the patient, medical professionals and even family members (such as parents). More generally, the handset 3 runs various software applications which help the user (and other authorised parties) to keep track of diet, insulin, blood glucose and exercise (which as explained above is recorded automatically from a sensor in the delivery device). By automating data collection, the handset 3 eliminates, or at least reduces, the need for a diabetes journal and ensures that comprehensive and accurate clinical information are constantly available to the patient and medical professionals via the server 4.

When controlling the delivery device, the handset 3 sends wireless signals to the delivery device 2 to deliver regular periodic doses of insulin at a pre-determined basal rate, which is set on the handset 3 according to the recommendations of a medical professional. The basal rate may be adjustable by the user within certain constraints. However, the software is configured such that it is not allowed for the basal rate to be adjusted remotely by third parties such as doctors. The hand-held device 3 also allows the user to trigger extraordinary bolus doses, for example after eating carbohydrates or performing exercise. As with a basal dose, the bolus dose is delivered by the delivery device 2 in response to control signals sent wirelessly from the handset 3. The user is able to input the volume of carbohydrates which have been consumed at a relevant time and is also able to input periods of exercise and the hand-held device is able to recommend adjustments to the basal rate or when a bolus is needed. As discussed above, the glucose monitor 32 may have an influence on the dosage. All of this information is transmitted to the server 4. The hand-held device 3 also receives information from the delivery device 2, for example to indicate whether it is faulty or when the insulin cartridge needs to be replaced. It also provides an indication of battery level.

Server

It will be understood from the above that the handset 3 and the delivery device 2 monitor and record clinical information while delivering insulin according to the body's needs. By providing this information to the server 4, it can be made almost immediately available to all those who need to see it. In particular, a mobile connection to a secure online management portal makes it possible for patients, clinicians and parents to be made constantly aware of, and able to react to, changing conditions. A diabetes clinic with patients using the system is able to see the current status of all its patients on a single screen, delivered to the clinic in real time. The portal can be accessed over the Internet in the clinic or through a smartphone. In addition to making it possible for a patient to access their latest clinical information online, it is possible for the patient to see simple visual analysis of their data, for example to identify trends and patterns in their blood sugar, and to immediately see their insulin dosing habits. This information can all be viewed using a simple online web portal that can be accessed from home, from work or from a smartphone. The server can also transmit SMS messages to a child's parents to let them know their child's information and state of health.

A patient using the system is provided with a personal login to the secure mobile diabetes management portal. Once logged in the patient can see all of their automatically collected data in the form of charts and graphs to help them understand where they might need to make adjustments. Exercise habits are mapped out in pie charts. An indication of exactly how and when the patient's insulin was delivered is provided. The patient's clinicians are able to see the same analysis and information, enabling them to call or text the patient whenever needed with guidance and advice.

From a single online dashboard screen, the clinic has access to the status of all the patients on the system; including current blood sugar, average blood sugar, insulin dosing, hypo frequency and blood testing habits. At a glance, anyone having difficulties can easily be identified for an immediate response. With a single click, all the data for a patient is analysed and charted to identify trends, patterns and problems. Using the portal, clinics can completely reorganise the way in which patients are managed. Text and email can be used to check on recent events. Clinic visits are focused completely on current and accurate information.

Releasable Cartridge

As described above, the delivery device 2 comprises two parts; a cartridge, which is intended to be disposable, and a device body, which is intended to be reusable. The cartridge comprises the reservoir, the valve arrangement and a pumping device, while the device body comprises a battery, control circuitry and a biasing spring and member. Occasionally, the insulin cartridge may develop a fault and go into free-flow (uncontrolled delivery of insulin to the patient), which may be dangerous if too much insulin is dispensed. An alarm is preferably provided on the handset, but the user may not hear this. In order to avoid the risk of an overdose, the cartridge is automatically released from the pump body in the event of a fault. As will be described below, the cartridge is engaged with the device body using catches, or clips (provided for example on the device body), which engage with corresponding lugs (provided for example on the cartridge), and these may be released upon detection of a fault. The bias applied by the biasing member (part of the device body) against the reservoir (part of the cartridge) serves to eject the cartridge safely away from the device body when the clips are released. The clips are normally held in situ by a wire element. In the event of a fault, current is passed through the wire element, whereupon the wire deforms and the clips are released, causing the cartridge to be ejected. As mentioned above, an alarm may be provided on the handset, triggered when the rate of delivery of insulin is too high. Preferably, too delivery rate thresholds are defined; a first, lower, threshold at which only an alarm is triggered, and a second, higher, threshold at which both the cartridge is ejected from the device body and an alarm is triggered at the handset to notify the patient of the ejection so that they can obtain and fit a new cartridge to the delivery device.

Referring to FIGS. 4A and 4B, an example releasable engagement mechanism is illustrated in both retained (FIG. 4A) and released (FIG. 4B) states. FIG. 4A shows the cartridge 26 and the device body 21 of the delivery device of FIG. 2. The cartridge 26 is engaged with the device body 21 via lugs 410 on the cartridge 26 which project into the device body 21 through apertures 405 to engage with clips 420 within the device body 21. The lugs 410 comprise a recessed part 412 (shown in FIG. 4B) into which a projecting part or edge of the clips 420 can be received to provide engagement. The clips 420 are movable between a retaining position (as shown in FIG. 4A) and a releasing position (as shown in FIG. 4B). Normally, the clips 420 are held in the retaining position shown in FIG. 4A by a spring 430. However, in the event of a fault being detected, an electric current is passed through a wire element (muscle wire) 440, which is attached to a sliding structure on which the clips are provided, and to a fixed mounting point 445 within the device body 21. The electric current causes the wire element 440 to contract, which pulls the sliding structure, and thus the clips 420, towards the fixed mounting point 445 against the bias provided by the spring 430. This causes the clips 420 to move out of engagement with the lugs 410, and into the position shown in FIG. 4B. The lugs 410 are unable to follow the movement of the clips 420, since they are constrained within the apertures 405 against lateral movement. As a result, the clips 420 are no longer positioned to prevent the lugs from being withdrawn out of the apertures 405. A spring 450 is visible in FIG. 4A. This is the biasing member of FIG. 2, and it can be seen that at one end it presses against the cartridge 26. While the clips 420 are engaged with the lugs 410, this biasing force is unable to separate the cartridge 26 from the device body 21, but once the clips 420 are no longer engaged with the lugs 410, the biasing force acts to separate the cartridge 26 from the device body, causing the lugs 410 to exit the device body 21 via the apertures 405, and the cartridge 26 to be forcibly ejected away from the device body 21. It is also possible for the sliding structure carrying the clips 420 to be moved manually by a user pressing a release actuator 460. The manual force provided by the user pressing inwardly on the release actuator 460 acts against the bias provided by the spring 430 in like manner to the wire element 440, causing the same disengagement of the clips 420 from the lugs 410 and separation of the cartridge 26 from the device body 21. In this way a user is able to remove an empty cartridge in order that a new cartridge can be fitted to the device body 21. It will be appreciated that, to engage a cartridge 26 with the device body 21, the cartridge 26 can be positioned so that its lugs 410 line up with the apertures 405 in the device body, and the cartridge 26 is then pressed against the device body 21. It will be seen from FIGS. 4A and 4B that the edges of the apertures 405 and the lugs are bevelled/chamfered to facilitate entry of the lugs 410 into the apertures, and also that the top portion of the clips 420 are bevelled/chamfered so that, when the lugs 410 are urged against the top portion of the clips 420 while the clips 420 are in the retaining position (which would block passage of the lugs 410), the sloped surfaces of the clips 420 and lugs 410 will cause the sliding structure to be deflected into the releasing position to allow the lugs 410 to pass the clips 410, whereupon the slips 420 will snap back into the retaining position to engage with the recessed part 412 of the lugs 410.

Referring to FIGS. 5A and 5B, these show the same elements as FIGS. 4A and 4B, but 3D view. Clearly visible in FIGS. 5A and 5B is the reservoir portion 470 of the cartridge 26, which is received within the device body 21. It can be seen that the spring 450 is received within the reservoir portion 470 of the cartridge 26 (as described above with reference to FIG. 2). When the clips 420 release the lugs 410, the force exerted by the spring 450 within the reservoir 470 acts to eject the cartridge 26 from the device body 21. It can also be seen more clearly from FIGS. 5A and 5B that the clips 420 and the sliding structure are formed as a single (preferably plastic) element which slides reciprocally within a channel (not shown).

Referring to FIG. 6, the detection of a fault and actuation of the ejection of the cartridge 26 from the device body 21 is schematically illustrated. A biasing member 610 acts against the base of an insulin reservoir of the cartridge 26 (as described in relation to FIG. 2). The rate at which the biasing member 610 moves is proportional and related to the rate of delivery of insulin from the cartridge 26 to the patient. The current position of the biasing element 610 is determined by a displacement sensor 620 which is mechanically coupled to the biasing element 610. The determined position of the biasing element is notified to control circuitry 630, which is powered by a battery 640, and which calculates from the determined position with respect to time, a rate of delivery of insulin to the patient. If the calculated rate of delivery exceeds a predetermined fault threshold, then the control circuitry 630 causes an electric current to be drawn from the battery 640 and applied to a wire element 650. The electric current causes the wire element 650 to contract, which moves a releasing element 660 from a retaining position to a releasing position. When this happens, the biasing force applied by the biasing element 610 acts against the cartridge 26 to release the cartridge 26 from the device body 21. In FIG. 6, solid lines denote electrical connection while dashed lines denote mechanical connection.

While embodiments of the present invention have been described with reference to an insulin delivery system, it will be appreciated that the present invention may be applied instead to the delivery of other drugs.

The invention claimed is:

1. A therapeutic product delivery device comprising:
a device body;
a cartridge for holding a therapeutic product;
an engagement structure for releasably engaging the cartridge with the device body the engagement structure comprising:
one or more first engaging elements on one or other of the device body and the cartridge, the first engaging elements being engagable with one or more corresponding second engaging elements on the other of the device body and the cartridge,
a releasing element which is moveable between a retaining position in which the first engaging elements are able to engage the second engaging elements, and a releasing position in which the first engaging elements are not able to engage with the second engaging elements, and
a wire element which is deformable in response to an applied electric current to move the releasing element from the retaining position to the releasing position;
a fault detector for detecting a fault in the delivery of the therapeutic product from the cartridge; and
a release trigger, responsive to the detection of a fault, to apply an electric current to the wire element, thereby deforming the wire element to cause the engagement structure to release the cartridge from the device body.

2. The therapeutic product delivery device according to claim 1, wherein the cartridge comprises a reservoir containing the therapeutic product and a pumping device for pumping the therapeutic product from the reservoir to the patient.

3. The therapeutic product delivery device according to claim 2, wherein
the device body comprises a biasing element which presses against the reservoir of the cartridge when the cartridge is engaged with the device body; and
the force exerted by the biasing element on the cartridge causes the cartridge to be ejected away from the device body when the engagement structure releases the cartridge from the device body.

4. The therapeutic product delivery device according to claim 3, wherein the biasing element comprises a spring.

5. The therapeutic product delivery device according to claim 1, wherein the first engaging elements are clips, and the second engaging elements are lugs.

6. The therapeutic product delivery device according to claim 1, wherein the engagement structure comprises a spring which biases the releasing element towards the retaining position, the wire element acting against the bias in response to the applied electric current to move the releasing element into the releasing position.

7. The therapeutic product delivery device according to claim 1, comprising a release actuator, responsive to user manipulation to move the releasing element from the retaining position to the releasing position.

8. The therapeutic product delivery device according to claim 1, wherein the fault detector detects a fault when a rate of delivery of the therapeutic product exceeds a predetermined threshold rate.

9. The therapeutic product delivery device according to claim 3, wherein the biasing element presses against a movable element of the reservoir, and the fault detector comprises a displacement sensor for detecting a position of the movable element and detection circuitry for detecting a fault when the position of the movable element changes at a rate above a predetermined threshold rate.

* * * * *